US008772581B2

(12) United States Patent
Avidov et al.

(10) Patent No.: US 8,772,581 B2
(45) Date of Patent: Jul. 8, 2014

(54) GENOMICALLY MULTIPLIED RAPESEED PLANTS, COMPOSITIONS DERIVED THEREFROM AND USES OF SAME

(75) Inventors: Amit Avidov, Kiryat-Tivon (IL); Alon Lerner, Moshav Sharona-Doar-Na Galil Tachton (IL)

(73) Assignee: Kaiima Bio Agritech Ltd., Kfar-Tavor (IL)

( * ) Notice: Subject to any disclaimer, the term of this patent is extended or adjusted under 35 U.S.C. 154(b) by 64 days.

(21) Appl. No.: 12/741,376

(22) PCT Filed: Nov. 6, 2008

(86) PCT No.: PCT/IL2008/001468
§ 371 (c)(1),
(2), (4) Date: May 5, 2010

(87) PCT Pub. No.: WO2009/060453
PCT Pub. Date: May 14, 2009

(65) Prior Publication Data
US 2011/0093967 A1    Apr. 21, 2011

Related U.S. Application Data

(60) Provisional application No. 60/996,213, filed on Nov. 6, 2007.

(51) Int. Cl.
*A01H 1/08* (2006.01)
*A01H 4/00* (2006.01)
*A01H 5/00* (2006.01)
*A01H 5/10* (2006.01)

(52) U.S. Cl.
USPC ............ 800/306; 800/260; 800/299; 435/430

(58) Field of Classification Search
None
See application file for complete search history.

(56) References Cited

U.S. PATENT DOCUMENTS

2013/0254913 A1    9/2013   Avidov et al.

FOREIGN PATENT DOCUMENTS

| JP | 63-084429 | 4/1988 |
|---|---|---|
| WO | WO 2009/060453 | 5/2009 |
| WO | WO 2009/060455 | 5/2009 |

OTHER PUBLICATIONS

Davis et al. Annals of Botany 77: 223-234 (1996).*
Appelqvist, L. Physiologia Plantarum 21(3): 615-625 issued 1968 (Abstract only).*
Office Action Dated Jan. 26, 2012 From the Israel Patent Office Re. Application No. 205557 and Its Translation Into English.
Office Action Dated Jan. 26, 2012 From the Israel Patent Office Re. Application No. 205558 and Its Translation Into English.
Restriction Official Action Dated Apr. 13, 2012 From the US Patent and Trademark Office Re. U.S. Appl. No. 12/741,599.
International Search Report Dated Mar. 4, 2009 From the International Searching Authority Re.: Application No. PCT/IL2008/001470.
International Search Report Dated Feb. 18, 2009 From the InternationalSearching Authority Re.: Application No. PCT/IL2008/001468.
Written Opinion Dated Mar. 4, 2009 From the International Searching Authority Re.: Application No. PCT/IL2008/001470.
Written Opinion Dated Feb. 18, 2009 From the International Searching Authority Re.: Application No. PCT/IL2008/001468.
International Preliminary Report on Patentability Dated May 20, 2010 From the International Bureau of WIPO Re.: Application No. PCT/IL2008/001468.
International Preliminary Report on Patentability Dated May 20, 2010 From the International Bureau of WIPO Re.: Application No. PCT/IL2008/001470.
Communication Pursuant to Article 94(3) EPC Dated Jan. 12, 2011 From the European Patent Office Re. Application No. 08846788.1.
Response Dated Jul. 11, 2011 to Communication Pursuant to Article 94(3) EPC of Jan. 12, 2011 From the European Patent Office Re. Application No. 08846788.1.
Response Dated Jul. 18, 2011 to Communication Pursuant to Article 94(3) EPC of Jan. 24, 2011 From the European Patent Office Re. Application No. 08848502.4.
Communication Pursuant to Article 94(3) EPC Dated Dec. 29, 2011 From the European Patent Office Re. Application No. 08848502.4.
Response Dated Aug. 1, 2011 to Communication Pursuant to Article 94(3) EPC of Jan. 24, 2011 From the European Patent Office Re. Application No. 08848502.4.
Communication Pursuant to Article 94(3) EPC Dated Feb. 10, 2012 From the European Patent Office Re. Application No. 08846788.1.
Communication Pursuant to Article 94(3) EPC Dated Jan. 24, 2011 From the European Patent Office Re. Application No. 08848502.4.
Restriction Official Action Dated Feb. 27, 2012 From the US Patent and Trademark Office Re. U.S. Appl. No. 12/741,376.
Notification About Necessity of Providing Additional Material Dated Jun. 12, 2012 From the Eurasian Patent Organization, The Eurasian Patent Office Re. Application No. 201000736 and Its Translation Into English.
Official Action Dated Jul. 13, 2012 From the US Patent and Trademark Office Re. U.S. Appl. No. 12/741,599.
Mederos Molina et al. "Micropropagation of Ricinus Communis", Journal of Plant Physiology, 147: 270-272, 1995.
Sidorov "Production of Tetraploids in Castor Oil Plant Ricinus Communis by the Action of Colchicine", Armyanskiy Khimicheskiy Zhurnal, 31(3): 264-265, 1941 and Its Translation Into English.
Translation of Office Action Dated Aug. 30, 2012 From the State Intellectual Property Office of the People's Republic of China Re. Application No. 200880124137.0.
Translation of Search Report Dated Aug. 30, 2012 From the State Intellectual Property Office of the People's Republic of China Re. Application No. 200880124137.0.
Chen et al. "Studies on Polyploid Induction of Tomato With Colchicine", Shandong Agricultural Sciences, 3: 22-24, 2007.
Translation of Office Action Dated Sep. 19, 2012 From the State Intellectual Property Office of the People's Republic of China Re. Application No. 200880124139.X.
Translation of Search Report Dated Sep. 19, 2012 From the State Intellectual Property Office of the People's Republic of China Re. Application No. 200880124139.X.
De et al. "Stability of Rape Genome", Journal of West Henan Agricultural College, 3: 49-53, 1990. Chinese Only!

(Continued)

*Primary Examiner* — David T Fox

(57) ABSTRACT

A rapeseed plant having a multiplied genome being at least as fertile as a euploid rapeseed plant isogenic to the genomically multiplied plant grown under similar conditions.

18 Claims, 8 Drawing Sheets
(7 of 8 Drawing Sheet(s) Filed in Color)

(56) References Cited

OTHER PUBLICATIONS

Zhou et al. "Studies on Efficient Production of Doubled Haploid Plants by Colchicine Treatments in Microspore Culture of *Brassica napus*", Agriculture Sciences in China, 35(4): 410-414, 2002. Chinese Only!
Ben-Ner "Multiplication of Genome. A Way to Improve Productivity of Energy Crops", BF-Agritech Ltd, 4 P., Nov. 2006.
Bhattacharya et al. "Effect of Magnetic Field on the Living Cells and Chromosomes", 6th Lowrad Conference, Budapest, Hungary, XP002515948, Oct. 17-20, 2007. Abstract.
BioFuel "BioFuel MS", BioFuel International Ltd., 2 P., Oct. 2007.
BioFuel "Sustainability—Multiplied", BioFuel international Ltd., 14 P., Oct. 2007.
BioFuel "XL Seed Change in Energy", BioFuel International Ltd., 1 P., Oct. 2007.
Kudo et al. "Flow Cytometric Evidence for Endopolyploidy in Seedlings of Some *Brassica* Species", Theoretical and Applied Genetics, XP009111736, 102(1): 104-110, Jan. 2001.
Moslikin "Genetics and Breeding of Castor. Cytology and Genetics of Qualitiative Characteristics", Castor, Chap.5: 93-133, 1986.
Osborn et al. "Understanding Mechanisms of Novel Gene Expression in Polyploids", Trends in Genetics, XP004411460, 19(3): 141-147, Mar. 1, 2003.
Tai et al. "Incomplete Bivalent Pairing in Dihaploids of *Brassica napus* L", Genome, XP001538976, 30(3): 450-457, 1988.
Timko et al. "Euploidy in Ricinus. Euploidy Effects on Photosynthetic Activity and Content of Chlorophyll-Proteins", Plant Physiology, XP002515947, 67: 1084-1089, 1981.
Timko et al. "Freeze-Fracture Architecture and Polypeptide Composition of Thylakoid Membranes From Euplid Ricinus Cells", Journal of Cell Science, XP002515946, 52: 167-181, 1981. Abstract, 'Materials and Methods'.
Zhou et al. "Efficient Production of Doubled Haploid Plants by Immediate Colchicine Treatment of Isolated Microspores in Winter *Brassica napus*", Plant Growth Regulation, XP009111834, 37(2): 185-192, Jun. 2002.
Notification of the Need for Additional Materials Dated Apr. 18, 2013 From the Eurasian Patent Organization, The Eurasian Patent Office Re. Application No. 201000737 and Its Summary in English.
Patent Examination Report Dated May 20, 2013 From the Australian Government, IP Australia Re. Application No. 2008326013.
Translation of Office Action Dated Jun. 8, 2013 From the State Intellectual Property Office of the People's Republic of China Re. Application No. 200880124139.X.
Translation of Office Action Dated Jun. 9, 2013 From the State Intellectual Property Office of the People's Republic of China Re. Application No. 200880124137.0.
Communication Pursuant to Article 94(3) EPC Dated Dec. 6, 2012 From the European Patent Office Re. Application No. 08848502.4.
Chen et al. "Studies on Polyploid Induction of Tomato With Colchicine", Shandong Agricultural Sciences, 3: 22-24, 2007. English Translation.
Summons to Attend Oral Proceedings Pursuant to Rule 115(1) EPC Dated May 31, 2013 From the European Patent Office Re. Application No. 08846788.1.
Notification About Necessity to Submit Additional Materials Dated Feb. 8, 2013 From the Eurasian Patent Organization, The Eurasian Patent Office Re. Application No. 201000736 and Its Summary in English.
European Search Report and the European Search Opinion Dated Feb. 28, 2013 From the European Patent Office Re. Application No. 13153253.3.
Office Action Dated Mar. 5, 2013 From the Israel Patent Office Re. Application No. 205558 and Its Translation Into English.
Official Action Dated Jan. 22, 2013 From the US Patent and Trademark Office Re. U.S. Appl. No. 12/741,599.
Preliminary Conclusion of Qualification Examination Dated Feb. 5, 2013 From the State Intellectual Property Service of Ukraine, Ukrainian Institute of Industrial Property Re. Application No. 201007076 and Its Summary in English.
Jakob "A Trisomic Male Castor Bean Plant", Journal of Heredity, 54(6): 292-296, 1963.
Timko et al. "Euploidy in Ricinus. I. Euploidy and Gene Dosage Effects on Cellular Proteins", Biochemical Genetics, 18(1/2): 171-183, 1980.
European Search Report and the European Search Opinion Dated Jul. 30, 2013 From the European Patent Office Re. Application No. 13151699.9.
Applicant-Initiated Interview Summary Dated Nov. 21, 2013 From the US Patent and Trademark Office Re. U.S. Appl. No. 12/741,599.
Notification About Necessity to Submit Additional Materials Dated Aug. 19, 2013 From the Eurasian Patent Organization, The Eurasian Patent Office Re. Application No. 201000736 and Its Summary in English.
Office Action Dated Aug. 18, 2013 From the Israel Patent Office Re. Application No. 205557 and Its Translation Into English.
Wikipedia "Colchicine", Wikipedia, the Free Encyclopedia, 8 P., Last Modified Sep. 16, 2013.
Preliminary Conclusion of Qualification Examination on Patentability Dated Sep. 9, 2013 From the State Intellectual Property Service of Ukraine, Ukrainian Institute of Industrial Property Re. Application No. 201007076 and Its Summary in English.
Communication Pursuant to Article 94(3) EPC Dated Dec. 2, 2013 From the European Patent Office Re. Application No. 13153253.3.
Notification of the Need to Submit Additional Materials Dated Nov. 13, 2013 From the Eurasian Patent Organization, The Eurasian Patent Office Re. Application No. 201000737 and Its Summary in English.
Zhou et al. "Increasing Embryogenesis and Doubling Efficiency by Immediate Colchicine Treatment of Isolated Microspores in Spring *Brassica napus*", Euphytica, XP009111664, 128(1):27-34, 2002.
Communication Pursuant to Article 94(3) EPC Dated Dec. 10, 2013 From the European Patent Office Re. Application No. 08848502.4.
Office Action Dated Feb. 8, 2014 From the State Intellectual Property Office of the People's Republic of China Re. Application No. 200880124139.X and Its Translation Into English.
Office Action Dated Feb. 10, 2014 From the State Intellectual Property Office of the People's Republic of China Re. Application No. 200880124137.0 and Its Translation Into English.
Official Action Dated Feb. 26, 2014 From U.S. Appl. No. 13/892,366.
Official Action Dated Feb. 26, 2014 From U.S. Appl. No. 14/149,845.
Official Action Dated Feb. 27, 2014 From U.S. Appl. No. 12/741,599.

\* cited by examiner

GENOMICALLY MULTIPLIED RAPESEED PLANTS, COMPOSITIONS DERIVED THEREFROM AND USES OF SAME

RELATED APPLICATIONS

This application claims the benefit of priority from U.S. Provisional Patent Application 60/996,213 filed Nov. 6, 2007, the content of which is incorporated by reference as if fully set forth herein.

FIELD AND BACKGROUND OF THE INVENTION

The present invention, in some embodiments thereof, relates to genomically multiplied rapeseed plants, compositions derived therefrom and uses of same.

Rapeseed (*Brassica napus*), also known as rape, oilseed rape, rapa, and (in the case of one particular group of cultivars) canola, is a bright yellow flowering member of the family Brassicaceae (mustard or cabbage family).

Rapeseed is grown for the production of animal feed, vegetable oil for human consumption, and biodiesel; leading producers include the European Union, Canada, the United States, Australia, China and India. In India, it is grown on 13% of cropped land. According to the United States Department of Agriculture, rapeseed was the third leading source of vegetable oil in the world in 2000, after soybean and oil palm, and also the world's second leading source of protein meal, although only one-fifth of the production of the leading soybean meal. World production is growing rapidly, with FAO reporting that 36 million tonnes of rapeseed was produced in the 2003-4 season, and 46 million tons in 2004-5.

The rapeseed is the valuable, harvested component of the crop. The crop is also grown as a winter-cover crop. It provides good coverage of the soil in winter, and limits nitrogen run-off. The plant is ploughed back in the soil or used as bedding. Processing of rapeseed for oil production provides rapeseed animal meal as a by-product. The by-product is a high-protein animal feed, competitive with soya. The feed is mostly employed for cattle feeding, but also for pigs and chickens (though less valuable for these). The meal has a very low content of the glucosinolates responsible for metabolism disruption in cattle and pigs. Rapeseed "oil cake" is also used as a fertilizer in China, and may be used for ornamentals, such as Bonsai, as well. Rapeseed leaves and stems are also edible, similar to those of the related bok choy or kale. Rapeseed is a heavy nectar producer, and honeybees produce a light colored, but peppery honey from it. Canola oil (or rapeseed oil) contains both omega-6 and omega-3 fatty acids in a ratio of 2:1 and is second only to flax oil in omega-3 fatty acid. Canola oil's proponents claim that it is one of the most heart-healthy oils and has been reported to reduce cholesterol levels, lower serum tryglyceride levels, and prevent hypercoagulation.

Rapeseed oil is used in the manufacture of biodiesel for powering motor vehicles. Biodiesel may be used in pure form in newer engines without engine damage, and is frequently combined with fossil-fuel diesel in ratios varying from 2% to 20% biodiesel. Formerly, owing to the costs of growing, crushing, and refining rapeseed biodiesel, rapeseed derived biodiesel cost more to produce than standard diesel fuel. Prices of rapeseed oil are at very high levels presently (start November 2005) owing to increased demand on rapeseed oil for this purpose. Rapeseed oil is the preferred oil stock for biodiesel production in most of Europe, partly because rapeseed produces more oil per unit of land area compared to other oil sources, such as soy beans.

Thus, rapeseed, is an important and valuable field crop. Therefore, a continuing goal of plant breeders is to develop stable, high yielding rapeseed cultivars that are agronomically sound. The reasons for this goal are obviously to maximize the amount of grain produced on the land used and to supply food for both animals and humans. To accomplish this goal, the rapeseed breeder must select and develop rapeseed plants that have the traits that result in superior cultivars.

To date, there are no tetraploid rapeseed varieties and the main obstacles seem to be genetic instability and absence of sufficient sexual fertility to achieve a commercially valuable hybrid.

Additional background art includes:

C. Möllers, M. C. M. Iqbal and G. Röbbelen; Efficient production of doubled haploid Brassica napus plants by colchicine treatment of microspores, Euphytica, Vol. 75, Numbers 1-2/January, 1994, Springer, Netherlands.

Zhang, G. Q.; Resynthesizing Brassica napus from interspecific hybridization between Brassica rapa and *B. oleracea* through ovary culture. *Euphytica* 140(3), 2004.

Robert T. Gaeta, J. Chris Pires, Federico Iniguez-Luy, Enrique Leon and Thomas C. Osborn; Genomic Changes in Resynthesized Brassica napus and Their Effect on Gene Expression and Phenotype; The Plant Cell 19:3403-3417. 2007.

SUMMARY OF THE INVENTION

According to an aspect of some embodiments of the present invention there is provided a rapeseed plant having a multiplied genome being at least as fertile as a euploid rapeseed plant isogenic to the genomically multiplied plant grown under similar conditions.

According to some embodiments of the invention, the fertility is determined by at least one of:
 number of seeds per plant;
 gamete fertility assay; and
 acetocarmine staining.

According to some embodiments of the invention, the plant exhibits genomic stability for at least 2 passages.

According to some embodiments of the invention, the plant has a seed weight exceeding that of the euploid rapeseed plant.

According to an aspect of some embodiments of the present invention there is provided a rapeseed plant as deposited under the Budapest treaty in NCIMB Ltd. and having Accession No. NCIMB 41592 *Brassica napus* 187-2-4N.

According to an aspect of some embodiments of the present invention there is provided a plant part of the rapeseed plant.

According to an aspect of some embodiments of the present invention there is provided a rapeseed oil produced from the plant or plant part.

According to an aspect of some embodiments of the present invention there is provided a rapeseed meal produced from the plant or plant part.

According to some embodiments of the invention, the plant part is a seed.

According to an aspect of some embodiments of the present invention there is provided an isolated regenerable cell of the rapeseed plant.

According to some embodiments of the invention, the cell exhibits genomic stability for at least 2 passages in culture.

According to some embodiments of the invention, the cell is from a meristem, pollen, a leaf, a root, a root tip, an anther, a pistil, a flower, a seed or a stem.

According to an aspect of some embodiments of the present invention there is provided a tissue culture comprising the regenerable cells.

According to an aspect of some embodiments of the present invention there is provided a method of producing seeds of rapeseed, comprising self-breeding or cross-breeding the plant.

According to an aspect of some embodiments of the present invention there is provided a method of producing rapeseed oil, the method comprising:

(a) harvesting seeds of the rapeseed plant or plant part; and (b) processing the seeds so as to produce the rapeseed oil.

According to an aspect of some embodiments of the present invention there is provided a method of generating a genomically multiplied rapeseed, the method comprising contacting seeds of the rapeseed with a G2/M cell cycle inhibitor under a magnetic field thereby generating the genetically multiplied rapeseed seeds.

According to some embodiments of the invention, the G2/M cell cycle inhibitor comprises a microtubule polymerization inhibitor.

According to some embodiments of the invention, the microtubule polymerization inhibitor is selected from the group consisting of colchicine, nocodazole, oryzaline, trifluraline and vinblastine sulphate.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1A:
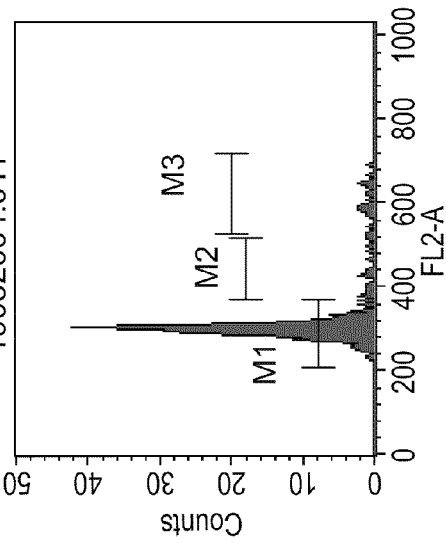
Figure 1B:
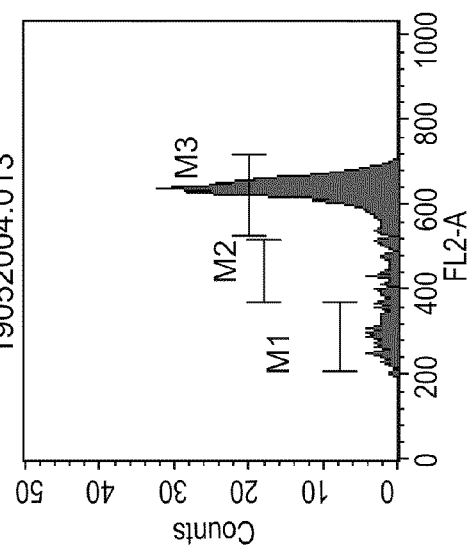
Figure 1C:
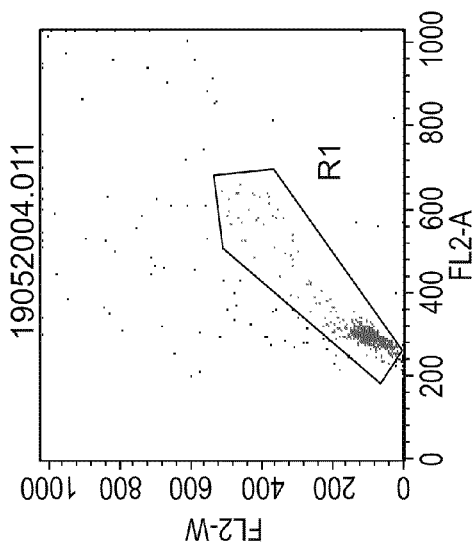
Figure 1D:
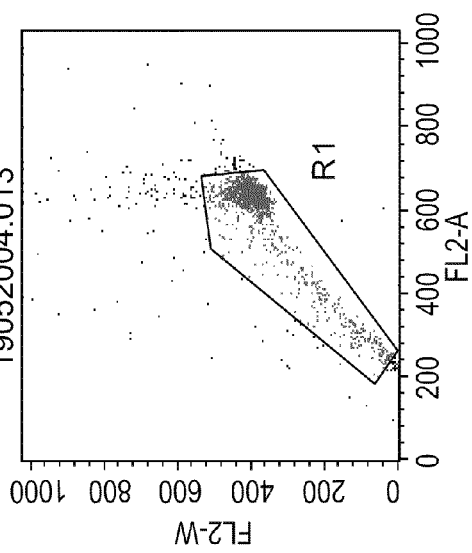

FIGS. 1A-D are FACS output images showing propidium iodide staining in a multiplied rapeseed plant (FIGS. 1C-D) vs control euploid plant (FIGS. 1A-B). An FL2 laser was used to detect the Propidium Iodide dye. Flow cytometer analysis displayed by histograms: one-parameter histogram that displays the distribution of cells according to their DNA content. The G1 phase of the non-multiplied plant positioned on channel 300 (M1). Second dot plot histogram shows that all the cells that belong to channel 300 are of the same size (FL2W). S phase of the cell cycle is marked as M2. On channel 600 appears the G2 of the cell cycle of the non-multiplied plant (M3). FIGS. 1C and 1D panels, the M3 region shows the G1 of the multiplied plant.

As is evident from the dot plot, the cells moved to 600 and show a bigger phenotype.

Figure 2:
Figure 3A:
Figure 3B:
Figure 3C:
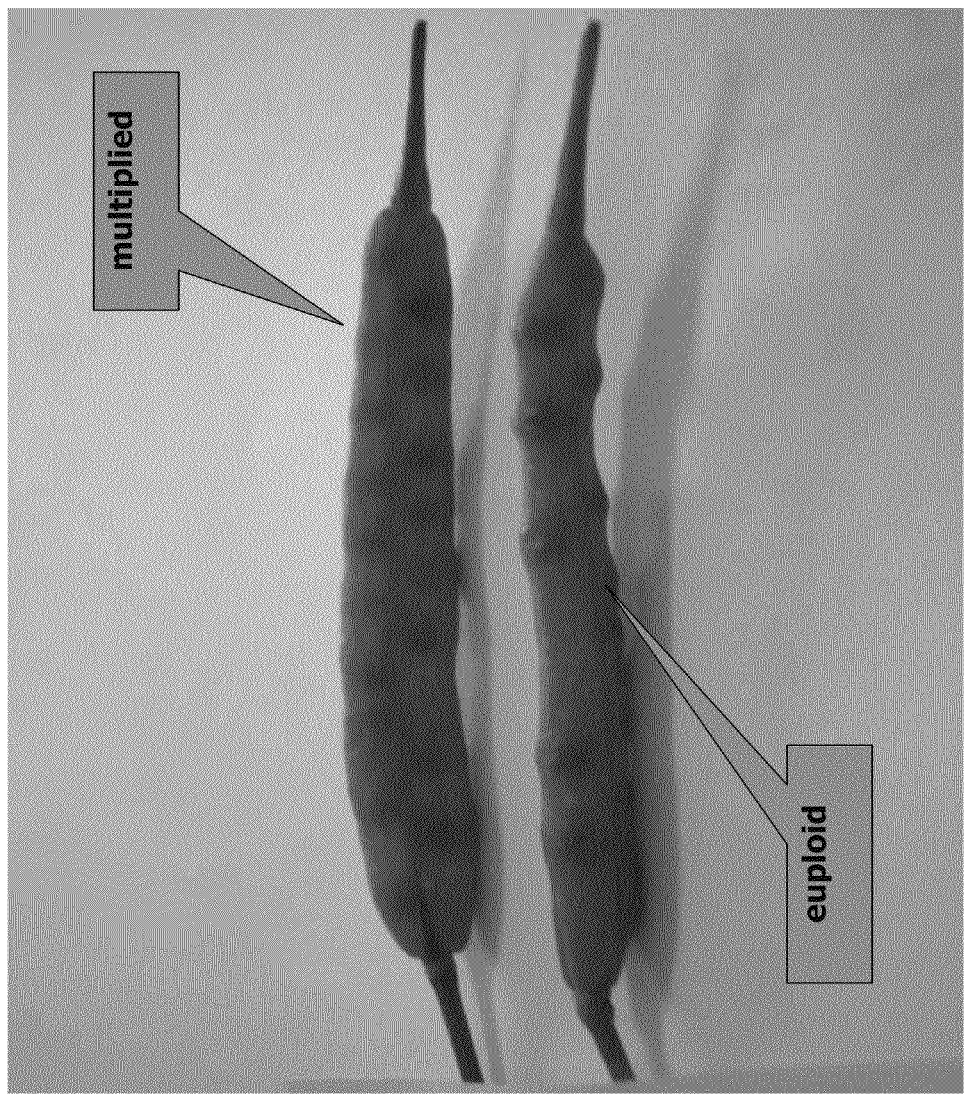
Figure 3D:
Figure 3E:
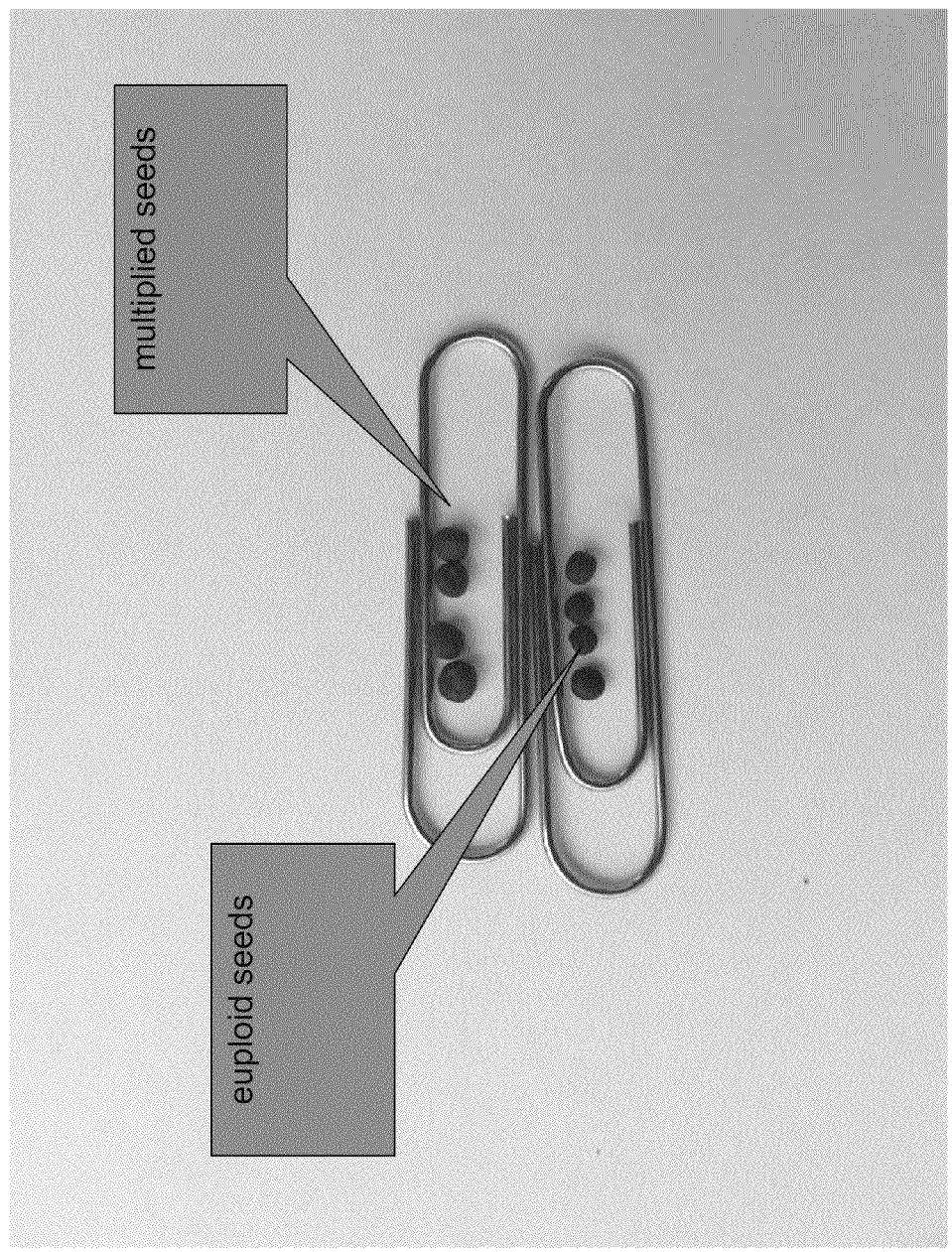
Figure 3F:
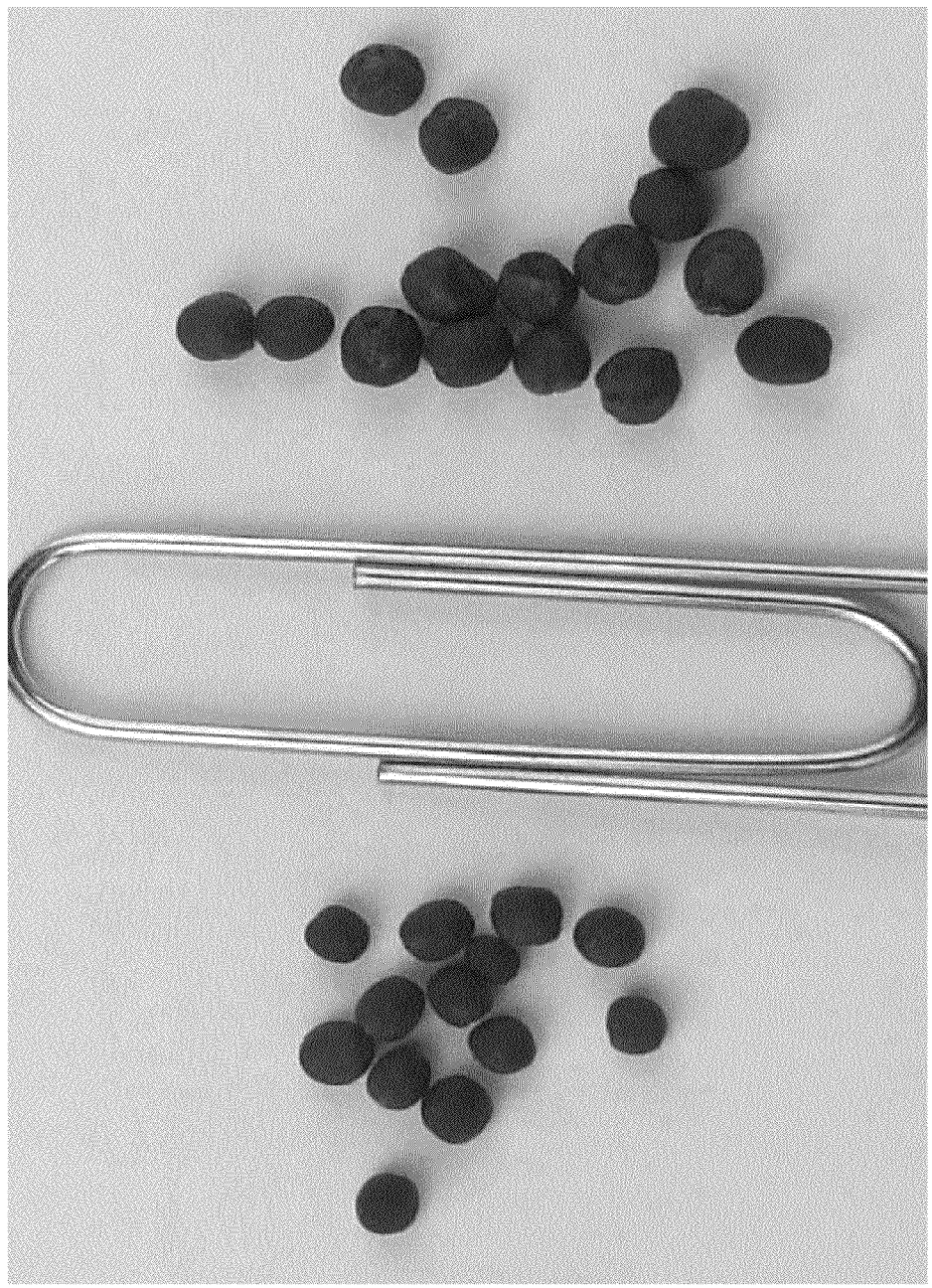

FIG. 2 is a table the statistics of the sterility trait in a hybrid between a multiplied male-sterile plant and a multiplied fully fertile plant.

FIGS. 3A-F are photographs showing the difference between the multiplied rapeseed generated according to the present teachings and the euploid plants in terms of pod size, number of seeds, seed size and flower size.

DESCRIPTION OF EMBODIMENTS OF THE INVENTION

The present invention, in some embodiments thereof, relates genomically multiplied rapeseed plants, compositions derived therefrom and uses of same.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Rapeseed is grown for the production of animal feed, vegetable oil for human consumption, and biodiesel. Leading producers include the European Union, Canada, the United States, Australia, China and India. In India, it is grown on 13% of cropped land. Over the years scientists have attempted to increase the overall oil content of the seed without compromising agronomic performance.

In order to meet these needs, the present inventors have identified conditions for genome multiplication in rapeseed plant seeds. Genomically multiplied rapeseed generated according to the present teachings provide for progeny plants characterized by as high a yield (e.g., seed yield, oil yield) and fertility as their isogenic euploid plants.

Thus, according to an aspect of the present invention there is provided a rapeseed plant having a multiplied genome being at least as fertile as a euploid rapeseed plant isogenic to the genomically multiplied plant grown under similar conditions.

As used herein the phrase "rapeseed plant" is the bright yellow flowering member of the family Brassicaceae (mustard or cabbage family) also termed as rape, oilseed rape, rapa, rapaseed and in the case of one particular group of cultivars, canola.

Rapeseed is a dibasic allotetraploid (i.e., amphidiploid) formed of two genomes (i.e., the A-genome and C-genome) and has a total of 38 chromosomes. The A-genome component is derived from *Brassica campestris* and consists of 20 chromosomes. The C-genome component is derived from *Brassica oleracea* and consists of 18 chromosomes. A rapeseed plant having the 38 chromosomes as described hereinabove is referred to herein as being euploid (i.e., non-multiplied). In some embodiments of the present invention the euploid plant is isogenic. The euploid plant, as used herein is isogenic to the multiplied plant i.e., the sets of chromosomes contain essentially identical alleles in all locations. The euploid plant may be naturally occurring, genetically modified or a breeding product.

The rapeseed plant of some embodiments of the present invention refers to a whole plant or portions thereof, processed or non-processed (e.g., seeds, oil, dry tissue, meal, cake etc.), regenerable tissue culture and cells isolated therefrom.

As used herein the term "multiplied genome" refers to a plant in which there is a higher (e.g., double) ploidy than in the isogenic euploid progenitor, that is a higher chromosome copy number than that of the euploid plant (e.g., 5N, 6N, 7N, 8N, 10N).

According to some embodiments of the present invention, the genomically multiplied plant is an autopolyploid i.e., the result of chromosome duplication.

As used herein the term "fertile" refers to the ability to reproduce sexually. Fertility can be assayed using methods which are well known in the art. The following parameters may be assayed in order to determine fertility: the number of seeds; gamete fertility may be determined by pollen germination such as on a sucrose substrate; and pollen fertility such as assayed microscopically using acetocarmine, whereby a fertile pollen is stained.

According to some embodiments of the present invention, a mature multiplied rapeseed plant has at least about the same (+/−10%) number of seeds as it's isogenic progenitor when grown under the same conditions; and optionally further has at least 90% fertile pollen that are stained by acetocarmine; and alternatively or additionally at least 90% of seeds germinate on sucrose.

Assays done for characterizing traits (e.g., fertility, yield, biomass and vigor) of the multiplied plants of the present invention, are typically effected in comparison to the isogenic progenitor (i.e., the euploid plant) being of the same developmental age as the tested plant and under similar growth conditions.

Thus, according to some embodiments of the present invention, the genomically multiplied plant has a larger surface area of a leaf than that of the euploid rapeseed plant. In exemplary embodiments leaf area: 30%-100% larger than that of the euploid plant and leaf thickness is at least 1.5-2.5 greater than that of the euploid plant.

According to some embodiments of the present invention, the genomically multiplied plant has a larger stomata surface than that of the euploid rapeseed plant. In an exemplary embodiment the stomata surface area is at least 1.5-2.5 greater than that of the euploid plant.

According to some embodiments of the present invention, the genomically multiplied plant is capable of cross-breeding with a euploid plant.

According to some embodiments of the present invention, the genomically multiplied has higher photosynthetic efficiency that the of the euploid plant.

According to some embodiments of the present invention, the genomically multiplied plant is stable for at least 4, 5, 7, 9 or 10 generations.

As used herein the term "stable" refers to the number of chromosomes or chromosome copies, which remains constant through several generations, while the plant exhibits no substantial decline in at least one of the following parameters: yield, fertility, biomass and vigor.

According to some embodiments of the present invention, the genomically multiplied plant has seed yield (as determined by at least one of: seed number, seed dimensions and volumetric oil content) at least as similar to an isogenic euploid plant grown under the same conditions and being of the same developmental age. According to further embodiments of the present invention, the seed yield exceeds that of the euploid plant by at least about 1.25, 1.5, 1.75, 2, 2.5 3 or 5 folds.

According to some embodiments of the present invention, the polyploid plant has seed yield (as determined by at least one of: seed number, seed dimensions and volumetric oil content) at least as similar to the isogenic euploid plant.

According to further embodiments of the present invention, the seed yield exceeds that of the euploid plant by at least about 1.15, 1.25, 1.5, 1.75, 2, 2.5, 3 or 5 folds.

According to further embodiments of the present invention, the seed weight exceeds that of the euploid plant by at least about 1.15, 1.25, 1.5, 1.75, 2, 2.5, 3 or 5 folds.

The plants of this aspect of the present invention can be generated using an improved method of colchicination, as follows.

Polyploid plants of the present invention can be generated using an improved method of colchicination, as described infra.

Germinating the seeds for 8 hours at a temperature of 27° C. in distilled water. Thereafter soaking the seeds in a multiplication solution comprising: 0.5% colchicine 0.5% DMSO, 0.03% Triton x 100 for 20 hours. Finally, the seeds are washed and seeded in an appropriate germination bed in 27° C.

Additionally or alternatively, multiplied rapeseed plants of the present invention can be generated using colchicine or any other cell cycle inhibitor (e.g., G2/M phase inhibitors, such as microtubule assembly inhibitors e.g., colchicine, vinblastine, nocodazole, oryzaline and trifluraline), whereby the targeting agent is a magnetic field for targeted delivery of the inhibitor to the chromatin fibers.

A specific embodiment of such a method is provided hereinbelow. Of note, measures are taken to maintain the indicated pH values each phase (such as with HCL or NaOH).

Stage One—3 Hours:

Seeds are incubated in a Petri dish at a temperature of 26° C. in the dark in a vinblastine sulphate (0.1% v/v) solution comprising 0.5% DMSO titrated to pH 5.6. pH conditions are monitored so as to maintain constant pH (5.6) throughout this phase.

The vessel is positioned in a magnetic field of 1300 Gauss, whereby the magnets are located 10.5 cm from each other.

Stage Two—3 Hours:

The seeds are incubated in the above solution in day-light conditions 4° C. and pH is titrated to 6.

Stage Three—6 Hours

The seeds are incubated in day-light conditions 20° C. and pH is titrated to 5.4.

Stage Four—12 Hours

The seeds are incubated in day-light conditions 26° C. and pH is titrated to 6. The magnetic field is removed and Nocodazole is added to a concentration of 5 m/ml.

Stage Five—12 Hours:

The seeds are incubated at day light under constant temperature conditions (26° C.).

The seeds are washed well in water so as to increase pH to 7. Thereafter, the seeds are seeded on appropriate growth beds under long-day light conditions (16 hours) 26° C.

Using the above teachings, the present inventors have established genetically multiplied rapeseed plants such as that deposited under the Budapest treaty in NCIMB Ltd. and having Accession No. NCIMB 41592 Brassica napus 187-2-4N.

Once established, the rapeseed plants of the present invention can be propagated sexually or asexually such as by using tissue culturing techniques.

As used herein the phrase "tissue culture" refers to plant cells or plant parts from which rapeseed plants can be generated, including plant protoplasts, plant cali, plant clumps, and plant cells that are intact in plants, or part of plants, such as seeds, leaves, stems, pollens, roots, root tips, anthers, ovules, petals, flowers, embryos, fibers and bolls.

According to some embodiments of the present invention, the cultured cells exhibit genomic stability for at least 2, 3, 4, 5, 7, 9 or 10 passages in culture.

Techniques of generating plant tissue culture and regenerating plants from tissue culture are well known in the art. For example, such techniques are set forth by Vasil., 1984. Cell Culture and Somatic Cell Genetics of Plants, Vol I, II, III, Laboratory Procedures and Their Applications, Academic Press, New York; Green et al., 1987. Plant Tissue and Cell Culture, Academic Press, New York; Weissbach and Weissbach. 1989. Methods for Plant Molecular Biology, Academic Press; Gelvin et al., 1990, Plant Molecular Biology Manual, Kluwer Academic Publishers; Evans et al., 1983, Handbook of Plant Cell Culture, MacMillian Publishing Company, New York; and Klee et al., 1987. Ann. Rev. of Plant Phys. 38:467 486.

The tissue culture can be generated from cells or protoplasts of a tissue selected from the group consisting of seeds, leaves, stems, pollens, roots, root tips, anthers, ovules, petals, flowers, embryos, fibers and bolls.

It will be appreciated that the plants of the present invention can also be used in plant breeding along with other rapeseed plants (i.e., self-breeding or cross breeding) in order to generate novel plants or plant lines which exhibit at least some of the characteristics of the rapeseed plants of the present invention.

Plants resultant from crossing any of these with another plant can be utilized in pedigree breeding, transformation and/or backcrossing to generate additional cultivars which exhibit the characteristics of the rapeseed plants of the present invention and any other desired traits. Screening techniques employing molecular or biochemical procedures well known in the art can be used to ensure that the important commercial characteristics sought after are preserved in each breeding generation.

The goal of backcrossing is to alter or substitute a single trait or characteristic in a recurrent parental line. To accomplish this, a single gene of the recurrent parental line is substituted or supplemented with the desired gene from the non-recurrent line, while retaining essentially all of the rest of the desired genes, and therefore the desired physiological and morphological constitution of the original line. The choice of the particular nonrecurrent parent will depend on the purpose of the backcross. One of the major purposes is to add some commercially desirable, agronomically important trait to the plant. The exact backcrossing protocol will depend on the characteristic or trait being altered or added to determine an appropriate testing protocol. Although backcrossing methods are simplified when the characteristic being transferred is a dominant allele, a recessive allele may also be transferred. In this instance, it may be necessary to introduce a test of the progeny to determine if the desired characteristic has been successfully transferred. Likewise, transgenes can be introduced into the plant using any of a variety of established transformation methods well-known to persons skilled in the art, such as: Gressel., 1985. Biotechnologically Conferring Herbicide Resistance in Crops: The Present Realities, In: Molecular Form and Function of the plant Genome, L van Vloten-Doting, (ed.), Plenum Press, New York; Huftner, S. L., et al., 1992, Revising Oversight of Genetically Modified Plants, Bio/Technology; Klee, H., et al., 1989, Plant Gene Vectors and Genetic Transformation: Plant Transformation Systems Based on the use of *Agrobacterium tumefaciens*, Cell Culture and Somatic Cell Genetics of Plants; and Koncz, C., et al. 1986, Molecular and General Genetics.

It will be appreciated that rapeseed plants (progenitor or multiplied) of the present invention can be genetically modified such as in order to introduce traits of interest e.g. Improved oil composition and enhanced resistance to stress (e.g., biotic or abiotic). Non-limiting examples of nucleic acid sequences useful for altering oil composition of rapeseed plants and methods of rapeseed transformation, as well as nucleic acid constructs useful for same are described in U.S. Pat. No. 6,974,893, which is hereby incorporated by reference in it's entirety.

According to some embodiments of the present invention the fatty acid composition of the multiplied rapeseed is about the same as that of the euploid rapeseed plant, although the level of the different components may vary.

Thus, the present invention provides novel rapeseed plants and cultivars, and seeds and tissue culture for generating same.

Rapeseed plants generated based on the present teachings can be further processed to generate rapeseed plant products which are commonly used in for numerous industrial applications, including animal feed, vegetable oil for human consumption, and biodiesel.

U.S. Pat. No. 6,441,278 provides exemplary methods for processing rapeseed and is hereby incorporated by reference in its entirety. Following is a non-limiting description. Rapeseed seed is collected and crushed by techniques known in the art. The seed typically is tempered by spraying the seed with water to raise the moisture to, for example, 8.5%. The tempered seed is flaked using smooth roller with, for example, a gap setting of 0.23 to 0.27 mm. Heat may be applied to the flakes to deactivate enzymes, facilitate further cell rupturing, coalesce the oil droplets and agglomerate protein particles in order to ease the extraction process.

Typically, oil is removed from the heated rapeseed flakes by a screw press to press out a major fraction of the oil from the flakes. The resulting press cake contains some residual oil.

Crude oil produced from the pressing operation typically is passed through a settling tank with a slotted wire drainage top to remove the solids expressed out with the oil in the screw pressing operation. The clarified oil can be passed through a plate and frame filter to remove the remaining fine solid particles.

Rapeseed press cake produced from the screw pressing operation can be extracted with commercial n-Hexane. The rapeseed oil recovered from the extraction process is combined with the clarified oil from the screw pressing operation, resulting in a blended crude oil.

Free fatty acids and gums typically are removed from the crude oil by heating in a batch refining tank to which food grade phosphoric acid has been added. The acid serves to convert the non-hydratable phosphatides to a hydratable form, and to chelate minor metals that are present in the crude oil. The phosphatides and the metal salts are removed from the oil along with the soapstock. The oil-acid mixture is treated with sodium hydroxide solution to neutralize the free fatty acids and the phosphoric acid in the acid-oil mixture. The neutralized free fatty acids, phosphatides and the like (soapstock) are drained off from the neutralized oil. A water wash may be done to further reduce the soap content of the oil. The oil may be bleached and deodorized before use, if desired, by techniques known in the art.

It is expected that during the life of a patent maturing from this application many relevant rapeseed products will be developed and the scope of the patent is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions, illustrate some embodiments of the invention in a non limiting fashion.

Example 1

Generation of Polyploid Rapeseed Plants

The Agricultural Academy of Anhui Province in China provided the two male parent lines (CHARO 1 and CHARO 8) and one female line with genetic sterility (CHAO 1). These parental lines underwent genome multiplication treatment using the mutation free genome multiplication (MFGM) technology according to any of the protocols described herein.

The treated plants underwent preliminary selection at the seedling stage and later were planted in a section protected by an insect net.

When the plants developed to the level of $5^{th}$ real leaf, they were all tested in a FACS machine (Fluorescence Activated Cell Sorter) for genome multiplication. Briefly, nuclei were released from 2 cm×2 cm leaf tissue by immersion in chopping buffer for 30 seconds.

Chopping buffer consisted of 4.575 gram $MgCl_2$, 2.095 gr.-MOPS, 4.4 gr-Sodium Citrate, 1 gr-DTT, 1.65 gr-Triton x 100 per 500 ml of distilled water. Chopping was done with a razor blade, in one direction. The chopped tissue was transferred tp Petri dish and placed on ice.

The sample was filtered before use (20 mesh). Nuclei samples (2 cc-6 cc) were removed to a FACS tube and 15 µl propidium iodide (PI) was added to each sample. Following 15 min, the samples were analysed in a flow cytometer fitted with a Cyonics argon laser (488 nm) operating at 15 mW.

Fluorescence that exceeded 635 nm is gated and results displayed as single parameter histograms of number of nuclei in each of 1024 channels. Control was fixed to channel 300.

FIGS. 1A-D show the output of a FACS machine for a control euploid plant versus a polyploid plant. All the genomically multiplied plants were tested for pollen fertility by germinating the pollen on a background containing sucrose solution.

Only the plants which pollen fertility was intact and the pollen grains appeared unharmed in a visual microscopic examination were left in the field for self pollination and for producing F1 hybrids. When the seeds matured, self-pollination seeds were collected from 50 multiplied plants from each of the two Chinese male varieties, the CHARO 1 and CHARO 8. These seeds were planted to test stability 2 generations and only the stable lines were kept for the remainder of the program. Hybridizations between all the fertile multiplied plants and between all the multiplied sterile plants from the CHAO 1 female line were effected.

Only the plants with the Aaaa genotype are capable of maintaining the sterile line and the distribution of the gametes of the Aaaa X aaaa cross is shown in FIG. 2.

All the hybridization offspring were planted for offspring tests in order to locate populations that divide 1:1 fertile and sterile.

In any such population the sterile plants are fertilized with pollen that are collected from the fertile plants in order to maintain the sterile line.

The hybrid tetraploid seeds were planted for a comparative yield test that included 4 repeats.

Example 2

Polyploid Fertility as Determined by Pollen Germination and Number of Pods

Rapeseed polyploids are known to have lower pollen fertility and therefore lower number of seeds in the pods. To test the fertility of polyploids generated according to the present teachings, the germination percentage and the number of seeds per pod in 2N canola populations were compared to the polyploids isogenic 4N line created by using the "MFGM" technology.

In the flowering period pollen was collected and germinated on sugar solution. Briefly, seeds were incubated on sucrose beds (2% sucrose and 2 mM $H_3BO_3$) for 12 hours in 26° C. Germination was evaluated thereafter. The germination percentage was calculated by counting the germinated pollen grains under a microscope. After full pods set up the seeds of all the 10 upper pods from the same plants were collected and counted.

Results:

TABLE 1

Pollen germination and number of seeds per pod (2N-non-multiplied; 4N-multiplied)

| 2N Line | Pollen germination % | Seeds Per Pods | 4N line | Pollen germination % | Seeds Per Pods |
|---|---|---|---|---|---|
| CHARO 1-1 | 92 | 17 | CHARO 1-1-2 | 94 | 19 |
| CHARO 1-2 | 94 | 15 | CHARO 1-1-3 | 94 | 18 |
| CHARO 1-3 | 93 | 20 | CHARO 1-1-4 | 97 | 16 |
| CHARO 1-4 | 94 | 19 | CHARO 1-1-5 | 96 | 17 |
| CHARO 1-5 | 95 | 17 | CHARO 1-1-6 | 96 | 18 |
| CHARO 1-6 | 97 | 18 | CHARO 1-11-1 | 93 | 19 |
| CHARO 1-7 | 95 | 16 | CHARO 1-11-2 | 95 | 17 |
| CHARO 1-8 | 93 | 19 | CHARO 1-11-3 | 94 | 15 |
| CHARO 1-9 | 94 | 18 | CHARO 1-11-4 | 94 | 15 |
| CHARO 1-10 | 94 | 17 | CHARO 1-11-5 | 93 | 20 |
| CHARO 1-11 | 95 | 15 | CHARO 1-11-6 | 95 | 21 |
| CHARO 1-12 | 96 | 18 | CHARO 1-11-7 | 95 | 17 |
| CHARO 1-13 | 95 | 19 | CHARO 1-11-8 | 94 | 18 |
| CHARO 1-14 | 94 | 20 | CHARO 3-5-8 | 92 | 18 |

Matched pair analyses showed that there was no significant difference between the number of seeds per pod and pollen germination percentage in the euploid plants and the isogenic multiplied plants.

Seed weight comparison between the multiplied plant and the isogenic euploid progenitor (CHARO1, Chao1) is provided in Table 2 below.

TABLE 2

| Field Number | Number of repeats | Number of seeds | Weight (gr) | Weight 1000 (gr) | |
|---|---|---|---|---|---|
| 3 | 1 | 40 | 0.274 | | |
|   | 2 | 40 | 0.259 | | |
|   | 3 | 40 | 0.263 | | |
|   | 4 | 40 | 0.255 | 6.56875 | 0.26275 |
| 5 | 1 | 40 | 0.195 | | |
|   | 2 | 40 | 0.187 | | |
|   | 3 | 40 | 0.183 | | |
|   | 4 | 40 | 0.183 | 4.675 | 0.187 |
| 23 | 1 | 40 | 0.251 | | |
|   | 2 | 40 | 0.252 | | |
|   | 3 | 40 | 0.25 | | |
|   | 4 | 40 | 0.242 | 6.21875 | 0.24875 |
| 49 | 1 | 40 | 0.248 | | |
|   | 2 | 40 | 0.247 | | |
|   | 3 | 40 | 0.252 | | |
|   | 4 | 40 | 0.247 | 6.2125 | 0.2485 |
| 81 | 1 | 40 | 0.237 | | |
|   | 2 | 40 | 0.23 | | |
|   | 3 | 40 | 0.219 | | |
|   | 4 | 40 | 0.227 | 5.70625 | 0.22825 |
| 82 | 1 | 40 | 0.25 | | |
|   | 2 | 40 | 0.225 | | |
|   | 3 | 40 | 0.244 | | |
|   | 4 | 40 | 0.229 | 5.925 | 0.237 |
| 98 | 1 | 40 | 0.235 | | |
|   | 1 | 40 | 0.233 | | |
|   | 1 | 40 | 0.224 | | |
|   | 1 | 40 | 0.237 | 5.80625 | 0.23225 |
| 99 | 1 | 40 | 0.225 | | |
|   | 2 | 40 | 0.224 | | |
|   | 3 | 40 | 0.208 | | |
|   | 4 | 40 | 0.221 | 5.4875 | 0.2195 |
| 289 | 1 | 40 | 0.224 | | |
|   | 2 | 40 | 0.235 | | |
|   | 3 | 40 | 0.238 | | |
|   | 4 | 40 | 0.237 | 5.8375 | 0.2335 |
| 290 | 1 | 40 | 0.248 | | |
|   | 2 | 40 | 0.239 | | |
|   | 3 | 40 | 0.244 | | |
|   | 4 | 40 | 0.237 | 6.05 | 0.242 |
| 291 | 1 | 40 | 0.222 | | |
|   | 2 | 40 | 0.217 | | |
|   | 3 | 40 | 0.218 | | |
|   | 4 | 40 | 0.197 | 5.3375 | 0.2135 |
| 292 | 1 | 40 | 0.235 | | |
|   | 2 | 40 | 0.24 | | |
|   | 3 | 40 | 0.232 | | |
|   | 4 | 40 | 0.252 | 5.99375 | 0.23975 |
| 293 | 1 | 40 | 0.222 | | |
|   | 2 | 40 | 0.225 | | |
|   | 3 | 40 | 0.217 | | |
|   | 4 | 40 | 0.245 | 5.68125 | 0.22725 |
| 294 | 1 | 40 | 0.228 | | |
|   | 2 | 40 | 0.233 | | |
|   | 3 | 40 | 0.238 | | |
|   | 4 | 40 | 0.24 | 5.86875 | 0.23475 |
| 295 | 1 | 40 | 0.244 | | |
|   | 2 | 40 | 0.228 | | |
|   | 3 | 40 | 0.253 | | |
|   | 4 | 40 | 0.235 | 6 | 0.24 |
| 296 | 1 | 40 | 0.162 | | |
|   | 2 | 40 | 0.168 | | |
|   | 3 | 40 | 0.154 | | |
|   | 4 | 40 | 0.161 | 4.03125 | 0.16125 |
| CHAR1 2n | 1 | 40 | 0.133 | | |
|   | 2 | 40 | 0.131 | | |
|   | 3 | 40 | 0.127 | | |
|   | 4 | 40 | 0.135 | 3.2875 | 0.1315 |
| Rapeseeds Chao1 2009 | 1 | 40 | 0.146 | | |
|   | 2 | 40 | 0.138 | | |
|   | 3 | 40 | 0.142 | | |
|   | 4 | 40 | 0.141 | 3.54375 | 0.14175 |

These results indicate that the multiplied lines are as fertile as the euploid lines.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCES

Other References are Cited Throughout the Application

Auger, D. L., Gray, A. D., Ream, T. S., Kato, A., Coe, E. H. J., & Birchler, J. A. (2005). Non-additive gene expression in diploid and triploid hybrids of maize. Genetics 169: 389-397.

Auger, D. L., Ream, T. S., & Birchler, J. A. (2004). A test for a metastable epigenetic component of heterosis using haploid induction in maize. Theor Appl Genet, 108(6), 1017-23.

Birchler, J. A., & Auger, D. L. (2004). Biological consequences of dosage dependent gene regulatory mechanisms in multicellular eukaryotes. In: Biology of Dominance. Ed. Veitia, R. Landes Bioscience.

Birchler, J. A., Auger, D. L., & Kato, A. (2004). Cytogenetics of corn. In: Corn: Origin, History, Technology and Production. Ed. Smith, C V, Betran, J, Runge, E. John Wiley and Sons, New York.

Birchler, J. A., Auger, D. L., & Riddle, N. C. (2003). In search of the molecular basis of heterosis. Plant Cell 15: 2236-2239

Birchler, J. A., Bhadra, U., Bhadra, M. P., & Auger, D. L. (2001). Dosage-dependent gene regulation in multicellular eukaryotes: implications for dosage compensation, aneuploid syndromes, and quantitative traits. Dev Biol, 234(2), 275-88.

Black, M. (2002). Statistical issues in the design and analysis of spotted microarray experiments. Ph.D. Dissertation, Department of Statistics, Purdue University, West Lafayette, Ind.

Black, M. A., & Doerge, R. W. (2002). Calculation of the minimum number of replicate spots required for detection of significant gene expression fold change in microarray experiments. Bioinformatics, 18(12), 1609-16.

Cao, D., Craig, B. A., & Doerge, R. W. 2005. A model selection based interval mapping method for autopolyploids. Genetics (published ahead of print on Jan. 31, 2005 as doi: 10.1534/Genetics. 104.035410)

Cao, D., Osborn, T. C. and Doerge, R. W. 2004. Correct estimation of preferential chromosome pairing in polyploids. Genome Research. 14:1-4.

Chen, Z. J., Wang, J., Tian, L., Lee, H. S., Wang, J. J., Chen, M., Lee, J. J., Josefsson, C., Madlung, A., Watson, B., Pires, J. C., Lippman, Z., Vaughn, M. W., Colot, V., Birchler, J. A., Doerge, R. W., Martienssen, R., Comai, L., & Osborn, T. (2004). The development of an *Arabidopsis* model system for genome-wide analysis of polyploidy effects. Biological Journal of the Linnean Society, 82, 689-700.

Comai, L. (2000). Genetic and epigenetic interactions in allopolyploid plants. Plant Mol Biol, 43(2-3), 387-99.

Comai, L., Tyagi, A. P., & Lysak, M. A. (2003). FISH analysis of meiosis in *Arabidopsis* allopolyploids. Chromosome Res, 11(3), 217-26.

Comai, L., Madlung, A., Josefsson, C., & Tyagi, A. (2003). Do the different parental 'heteromes' cause genomic shock in newly formed allopolyploids. Philos Trans R Soc Lond B Biol Sci, 358(1434), 1149-55.

Craig, B. A., Black, M. A., & Doerge, R. W. (2003). Gene Expression Data: The technology and statistical analysis. Journal of Agricultural, Biological and Environmental Statistics, 8(1), 1-28.

Dilkes, P. B., and L. Comai. 2004. A differential dosage hypothesis for parental effects in seed development. Plant Cell 16: 3174-3180.

Dilkes, B., Dobrozsi, S., Scott, R., & Comai, L. The Col blooded killer phenotype: a lethal paternal effect in interploidy crosses. In preparation.

Doerge, R. W. (2002). Mapping and analysis of quantitative trait loci in experimental populations. Nature Reviews Genetics, 3(1), 43-52.

What is claimed is:

1. A *Brassica napus* rapeseed plant having a doubled amphidiploid genome being at least as fertile as a euploid *Brassica napus* rapeseed plant isogenic to the genomically doubled plant grown under similar conditions, wherein fertility is determined by number of seeds per plant, and wherein the genomically doubled plant is grown from genomically doubled rapeseed seed, which seed have been generated by:
    (a) applying a magnetic field to seeds of the euploid *Brassica napus*; and
    (b) contacting said seeds of the euploid *Brassica napus* with a microtubule polymerization inhibitor under said magnetic field for targeted delivery of said microtubule polymerization inhibitor to chromatin fibers in nuclei of said seeds.

2. The plant of claim 1, exhibiting genomic stability for at least 2 generations.

3. The plant of claim 1, having a seed weight per 40 seeds exceeding that of said euploid rapeseed plant.

4. A rapeseed plant as deposited under the Budapest treaty in NCIMB Ltd. and having Accession No. NCIMB 41592 *Brassica napus* 187-24N.

5. A plant part of the rapeseed plant of claim 1.

6. Rapeseed meal produced from the plant of claim 1.

7. THE plant part of claim 5 being a seed.

8. An isolated regenerable cell of the rapeseed plant of claim 1.

9. The cell of claim 8, exhibiting genomic stability for at least 2 generations in culture.

10. The cell of claim 8 being from a meristem, pollen, a leaf, a root, a root tip, an anther, a pistil, a flower, a seed or a stem.

11. A tissue culture comprising the regenerable cell of claim 8.

12. A method of producing seeds of rapeseed, comprising self-breeding or cross-breeding the plant of claim 1.

13. A method of producing rapeseed oil, the method comprising:
    (a) harvesting seeds of the rapeseed plant of claim 1; and
    (b) processing said seeds so as to produce the rapeseed oil.

14. A method of generating a genomically doubled *Brassica napus* rapeseed seed, the method comprising:
   (a) applying a magnetic field to seeds of a euploid *Brassica napus*; and
   (b) contacting said seeds of said euploid *Brassica napus* with a G2/M cell cycle inhibitor comprising a microtubule polymerization inhibitor under said magnetic field for targeted delivery of said microtubule polymerization inhibitor to chromatin fibers in nuclei of said seeds;
   thereby generating the genomically doubled *Brassica napus* rapeseed seed.

15. The method of claim 14, wherein said microtubule polymerization inhibitor is selected from the group consisting of colchicine, nocodazole, oryzaline, trifluraline and vinblastine sulphate.

16. A tissue culture comprising the regenerable cell of claim 10.

17. The plant of claim 1, wherein said microtubule polymerization inhibitor is selected from the group consisting of colchicine, nocodazole, oryzaline, trifluraline and vinblastine sulphate.

18. The plant part of claim 7, wherein said seed is a hybrid seed.

* * * * *